US008172900B2

(12) United States Patent
Roberts et al.

(10) Patent No.: US 8,172,900 B2
(45) Date of Patent: May 8, 2012

(54) MICROSENSOR SYSTEM FOR APPLICATION IN BIOMECHANICS

(75) Inventors: Cynthia J. Roberts, Columbus, OH (US); Grant A. McCallum, Cleveland Heights, OH (US)

(73) Assignee: The Ohio State University, Columbus, OH (US)

( * ) Notice: Subject to any disclaimer, the term of this patent is extended or adjusted under 35 U.S.C. 154(b) by 966 days.

(21) Appl. No.: 11/663,362

(22) PCT Filed: Sep. 21, 2005

(86) PCT No.: PCT/US2005/033802
§ 371 (c)(1), (2), (4) Date: Sep. 24, 2007

(87) PCT Pub. No.: WO2006/034336
PCT Pub. Date: Mar. 30, 2006

(65) Prior Publication Data
US 2008/0177170 A1 Jul. 24, 2008

Related U.S. Application Data

(63) Continuation of application No. PCT/US05/33802, filed on Sep. 21, 2005.

(60) Provisional application No. 60/611,828, filed on Sep. 21, 2004.

(51) Int. Cl.
*A61F 2/16* (2006.01)
(52) U.S. Cl. ....... 623/6.22; 623/6.11; 623/4.1; 606/107; 600/407; 600/409

(58) Field of Classification Search ............... 623/6.22, 623/6.11, 4.1; 606/107; 600/407, 409
See application file for complete search history.

(56) References Cited

U.S. PATENT DOCUMENTS

| 4,622,644 | A | | 11/1986 | Hansen | |
|---|---|---|---|---|---|
| 5,562,731 | A | * | 10/1996 | Cumming | 606/107 |
| 6,645,245 | B1 | * | 11/2003 | Preussner | 623/6.22 |
| 7,090,696 | B2 | * | 8/2006 | Shahinpoor et al. | 623/4.1 |
| 7,441,559 | B2 | * | 10/2008 | Nelson et al. | 128/848 |
| 2004/0167587 | A1 | * | 8/2004 | Thompson | 607/60 |

(Continued)

FOREIGN PATENT DOCUMENTS

BG 37208 12/1983

OTHER PUBLICATIONS

International Search Report, PCT/US2005/033802, mailed Feb. 8, 2006 (5 pages).

(Continued)

*Primary Examiner* — Tse Chen
*Assistant Examiner* — Baisakhi Roy
(74) *Attorney, Agent, or Firm* — Dinsmore & Shohl, LLP

(57) ABSTRACT

A sensing system and method to detect and determine magnitude and direction of ciliary body movement within an eye of a patient is disclosed. The invention comprises a permanent magnet (PM) positioned in the ciliary body, and a sensing device (SD) positioned adjacent the ciliary body and configured to detect displacement of the permanent magnet relative to the sensing device via movement of the ciliary body. The invention also comprises a data processing device (DPD) configured to determine magnitude and direction of the ciliary body movement based on the displacement of the permanent magnet detected by the sensing device.

21 Claims, 3 Drawing Sheets

U.S. PATENT DOCUMENTS

2006/0089712 A1* 4/2006 Malecaze ................. 623/6.11

OTHER PUBLICATIONS

Written Opinion, PCT/US2005/033802, mailed Feb. 8, 2006 (6 pages).
Examination Report, EP 05799576.3, dated Aug. 6, 2009 (4 pages).
Hamiel, Steven et al., "Evaluation of the Hall-effect sensor for determination of eyelid closure in vivo," Otolaryngol Head Neck Surg, vol. 113, No. 1, pp. 88-91 (Jul. 1995).
Kaiser, et al., "A low-power transponder IC for high-performance identification systems," IEEE J. Solid-state Circuits, 30:306-310 (1995).
Kim, Keun Young et al, "A wireless measurement system for three dimensional ocular movement using the magnetic contact lens sensing technique," Proceedings of the 26th International Conference of the IEEE EMBS, vol. 3., pp. 2287-2289 (Sep. 2004).
Rodriguez, F et al., "Eye movement recording in freely moving animals," Physiology & Behavior, 72 (4): 455-460 (Mar. 2001).
Roumenin et al., "Five-contact silicon structure based integrated 3D Hall sensor," IEE-Electronic Letters Online No. 20031075 (2003).
Schlageter, V et al., "Tracking System with five degrees of freedom using a 2D-array of Hall sensors and a permanent magnet," Sensors and Actuators A, 92:37-42 (Dec. 2000).
Schott and Popovic, "Integrated 3D Hall magnetic field sensor," Transucers '99, Sendai, Japan, vol. 1, pp. 168-171 (Jun. 1999).
Stachs et al., "Monitoring accommodative ciliary muscle function using three-dimensional ultrasound," Graefe's Arch Clin Exp Ophthalmol, 240:906-912 (2002).
Stangel, et al., "A Programmable Intraocular CMOS Pressure Sensor System Implant," IEEE J. Solid-state Circuits, 36(7):1094-1100 (2001).

* cited by examiner

MICROSENSOR SYSTEM FOR APPLICATION IN BIOMECHANICS

CROSS-REFERENCE TO RELATED APPLICATIONS

This application is the National Stage Entry of International Application No. PCT/US05/33802, filed Sep. 21, 2005, which claims the benefit of U.S. Provisional Application Ser. No. 60/611,828, filed Sep. 21, 2004.

The present invention relates to a biomechanical microsensor system, and in particular, to a biomechanical microsensor system capable of dynamic measuring and recording of tissue motion in physiologic processes and surgical procedures.

Dynamic position, velocity and acceleration investigations of the human body are typically done on the macroscale. Such investigations include the head, joints, limbs, spinal column and eye movements. With the advances in semiconductor fabrication, highly sensitive, microscale sensors can be created to detect minute position changes by utilizing the Hall Effect, the well-known property of conducting materials. The Hall Effect and other microfabrication techniques can be used to create highly sensitive, microscale position sensors to detect minute changes in biological tissue.

The Hall Effect results from an exerted force on charged particles while moving through a conducting medium and subject to an external magnetic field. This force leads to an induced electric field resulting in a voltage differential, called Hall Voltage, that can be measured. A constant supply voltage, $V_x$, produces a current, $I_x$, which flows through the semiconductor material in the x direction. A magnetic field, $B_z$, passes through the semiconductor material in a direction that is perpendicular to the current flow.

According to the Lorentz force ($F=qE+qv \times B$), a charged particle moving through a magnetic field will experience a force upon in a direction that is perpendicular to both the particle's velocity and the magnetic field. This results in an induced electrical field ($E_H$) in the y-direction and produces a voltage across the semiconductor material called the Hall Voltage, $V_H$. The Hall Voltage is proportional to the current, $I_x$, and the strength of the magnetic field, $B_x$. Therefore, if the current is kept constant, the Hall Voltage will be a measure of the magnetic field strength experienced by the device.

Although the Hall Effect was described in only one dimension, the concept can be expanded to simultaneously measure the magnetic strength in all three dimensions $B_x$, $B_y$ and $B_z$. Microfabrication techniques in semiconductor device design enable integrated, multi-component designs to facilitate a three-dimensional magnetic field sensor. Since the magnetic field intensity decreases as a function of distance from the magnet, if the magnetic field direction and magnitude is known, the position of the magnet relative to the sensor at any point in time can be determined.

One area that such micro-measurements would be beneficial is ophthalmology. Biological eye accommodation, or the eye's ability to dynamically change the optics of the visual system for far or near vision, results from the interaction of three main components within the eye. FIG. 1a illustrates a cross-section schematic of the entire human eye. The interactions between the ciliary body, zonules and lens enable accommodation to occur. The ciliary body is a ring-shaped structure which lies outside the equatorial plane of the lens. When viewed in cross-section, it has a triangular-shape with the apex near the posterior portion of the eye and the base located more anterior near the iris and lens. A circumlental gap exists between the ciliary body and the lens. Within this gap are numerous, thin, elastic fibers called zonules which attach to the ciliary body at one end and the other end to the lens capsule.

The most widely accepted view of the human accommodation mechanism is that of Helmholtz. Briefly summarized, during accommodation, the ciliary body contracts and displaces in an anterior and sphincter-like motion toward the lens. This motion causes reduced tension on the zonules, thereby reducing the forces on the lens capsule, and ultimately causing the lens to increase in central thickness and optical power. During disaccommodation, the ciliary moves away from the lens and posteriorly. This places tension on the zonules causing the lens capsule to flatten the lens surface.

The ciliary body displacement has been found not to decrease during maximum accommodative efforts for eyes that are between the ages of 15 and 45. Presbyopia, the loss of accommodative ability, still occurs even though this displacement remains constant. This has been shown to be due to the increasing rigidity of the lens especially in the lens nucleus. To correct for this loss of accommodative ability, many intraocular lens (IOL) designs have been created which change linear position based on ciliary body movement. The anterior-posterior displacement changes the optics of the visual system causing a wider range in accommodative ability.

It is against that above background, that the present inventors have recognized a need to provide a microsensor system with the ability to sense the ciliary body movement in the eye and to generate a corresponding electrical signal that defines its characteristics. It is envisioned that such an electric signal can be used as a feedback control signal to intraocular devices to restore accommodative range and function of ciliary body movement in the eye.

Further, the microsensor system would also be beneficial in the treatment of gastric acid reflux. Gastric acid reflux is the condition where the lower esophageal sphincter does not close completely and the stomach acid passes into the lower esophagus, leading to heartburn and, in extreme cases, ulceration, scarring or perforation of the lower esophagus. Placing a microsensor on the sphincter, a physician would be able to tell if the sphincter has been open for a duration longer than required to allow food to pass into the stomach. If so, the microsensor system could electrically stimulate the sphincter to close, thereby reducing the occurrence of gastric reflux.

Accordingly, the present inventors have recognized a need for a microsensor system to measure movement and calculate dynamically the velocity and acceleration of physiological systems that can be incorporated in to biomedical instruments for diagnostic/therapeutic purposes as well as surgical instruments to produce superior patient outcomes. Further, they have recognized an additional need for a microsensor system that can be used to determine biomechanical tissue properties at the micro scale.

According to one embodiment of the present invention, a microsensor system that is adapted to ascertain tissue movements and calculate, in real-time, the velocity and acceleration of these minute movements is disclosed. The system comprises three components: a sensing device, a permanent magnet and a data processing device. The permanent magnet is inserted into, or on, the tissue that position changes are of interest. The sensing device is placed near the magnet but is fixed in place so that the sensing device will not move in unison with the magnet. As the tissue moves, the magnetic field orientation will change with respect to the sensing device. The sensing device will be able to detect and measure the three-dimensional magnitude and orientation changes and produce signals to be sent to the data processing device for further processing to determine the magnets position in space. Since the magnetic field sensor can be fabricated out of standard microelectric materials, integration of other functions such as analog-to-digital converters and digital signal processing can easily be incorporated on a single device.

In accordance with one embodiment of the present invention, the microsensor system has the ability to sense the onset of ciliary body movement in the eye including the magnitude and direction of its displacement.

In accordance with another embodiment of the present invention, the microsensor system has the ability to sense the opening and closing of lower esophageal sphincter.

Accordingly, the present invention dynamically senses micro-movement of biological tissues and calculate, in real-time, the velocity and acceleration of these movements.

In one specific application, the present invention senses the ciliary body movement in the eye and to generate a corresponding electrical signal that defines its characteristics, thereby leading to diagnostic determinations of proper IOL selection for implantation as well as a feedback control signal to intraocular devices to restore accommodative range and function.

In another specific application, the present invention senses the duration of that the lower esophageal sphincter remains open during digestion in order to diagnosis and treat gastric acid reflux disease.

Accordingly, a sensing system to detect and determine magnitude and direction of ciliary body movement within an eye of a patient is disclosed. The system comprises a permanent magnet (PM) positioned in the ciliary body, and a sensing device (SD) positioned adjacent the ciliary body and configured to detect displacement of the permanent magnet relative to the sensing device via movement of the ciliary body. The system also comprises a data processing device (DPD) configured to determine magnitude and direction of the ciliary body movement based on the displacement of the permanent magnet detected by the sensing device.

In addition, a method of detecting and determining magnitude and direction of ciliary body movement within an eye of a patient is disclosed. The method comprises positioning a permanent magnet (PM) in the ciliary body, and positioning a sensing device (SD) adjacent the ciliary body. The method further comprises detecting displacement of the permanent magnet relative to the sensing device via movement of the ciliary body, and using a data processing device to determine magnitude and direction of the ciliary body movement based on the displacement of the permanent magnet detected by the sensing device.

Other advantages and features of the present invention will be apparent in light of the description of the invention embodied herein.

The following detailed description of specific embodiments of the present invention can be best understood when read in conjunction with the following drawings, where like structure is indicated with like reference numerals and in which.

The sensing system is composed of three functional devices, a permanent magnet (PM), sensing device (SD) and data processing device (DPD). The following describes the properties, function and location for each of these system devices to detect and determine the magnitude and direction of ciliary body displacement of the eye.

Permanent Magnet (PM)

Figure 1A:
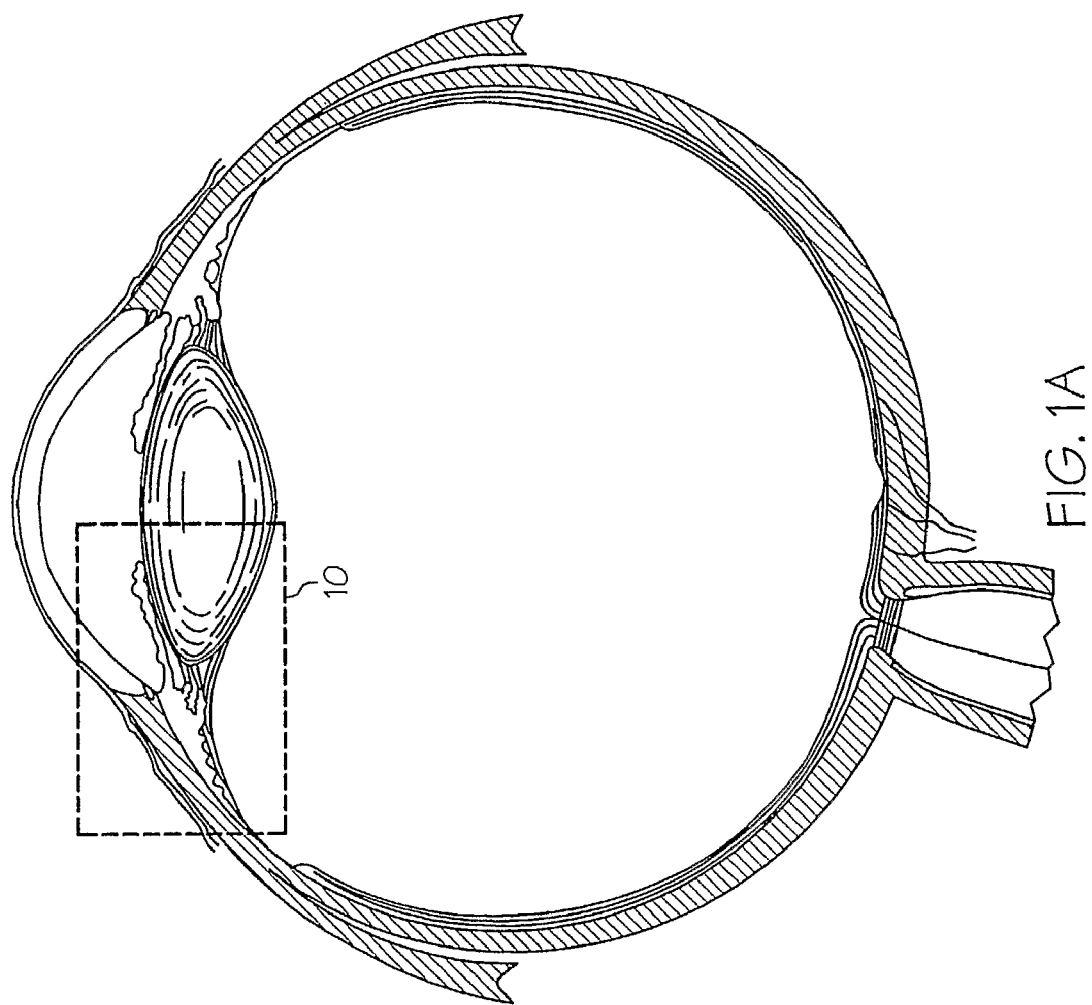
FIG. 1A illustrates a cross-section schematic of the entire human eye.
Figure 1B:
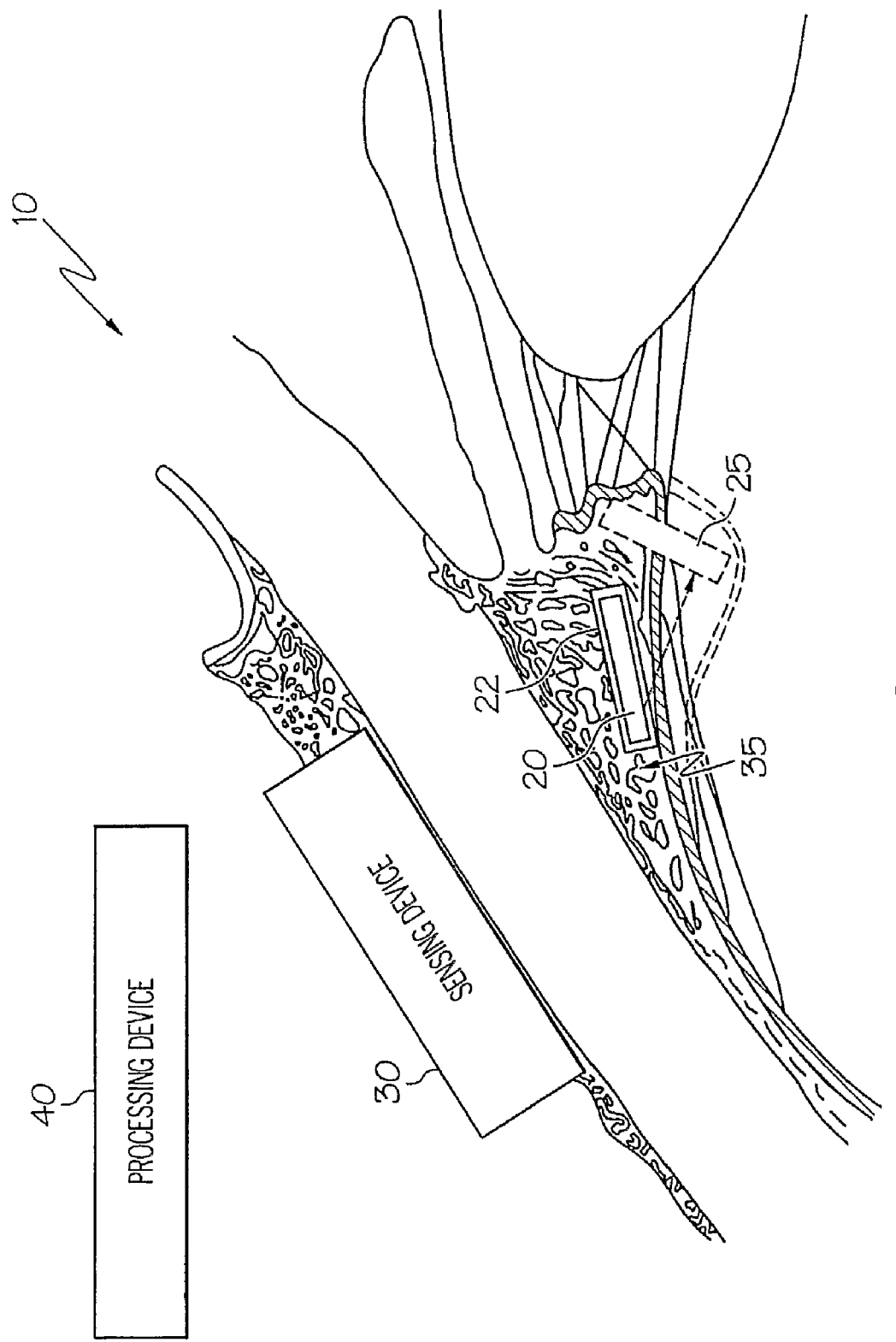
FIG. 1B illustrates the boxed section in FIG. 1A incorporating the microsensor system according to one embodiment of the present invention.

FIG. 1A illustrates a cross-section schematic of the entire human eye. FIG. 1B is a larger scale drawing of the boxed section 10 in FIG. 1B to provide more detail. FIG. 1B illustrates the parts of the ciliary body and the possible placement locations of the sensing system's components. Solid object 20 is a magnet position during disaccommodation of ciliary body 35 and the cross-hatched object 25 is the magnet's position during accommodation. A partial outline of the ciliary body 35 during accommodation is illustrated in dashed lines.

A magnetic field will be created by imbedding a rare-earth permanent magnet(s) 20 in the ciliary body 35 (as illustrated in FIG. 1B) between the circular fibers of the ciliary muscle and the ciliary processes. This placement location will result in the greatest displacement of the magnet(s) 20 relative to the sensor during accommodation. A three-dimensional ultrasound measurement study found the total resultant displacement, at this location, ranges from 0.28 mm to 0.51 mm. It is also envisioned that the magnet(s) 20 could be implanted into many other physiological systems such as, for example, the digestive system to help diagnosis and treat gastric acid reflux disease.

Permanent rare-earth magnets 20 possess high-energy products and stable magnetic fields which are important to increase the sensitivity of the sensing device 30. Rare-earth magnets 20, however, are susceptible to oxidation which over time will degrade their performance by reducing the working volume of the magnet. To eliminate the oxidation process, a 10-20 μm thick coating of nickel, zinc or aluminum can be applied to the magnet surfaces. The rare-earth magnet(s) 20 implanted in this system will be coated with a thin layer of biocompatible material to eliminate oxidation and adverse effects to the ciliary body tissue.

The rare-earth magnet(s) 20 used in this system will have single or multiple magnetic orientations resulting in a fixed magnetic field with regard to a single magnet plane or axis. As the ciliary body moves during accommodation, the magnet(s) 20 will be displaced by the same amount and direction. The magnetic field, however, will remain identical with respect to the magnet(s) 20 but will change with respect to the sensing device(s) 30. Being able to determine the component, three-dimensional magnetic field orientations and magnitudes, the position of the magnet(s) 20 relative to the sensor(s) 30 can be determined at any point in time.

Sensing Device (SD)

Figure 2:
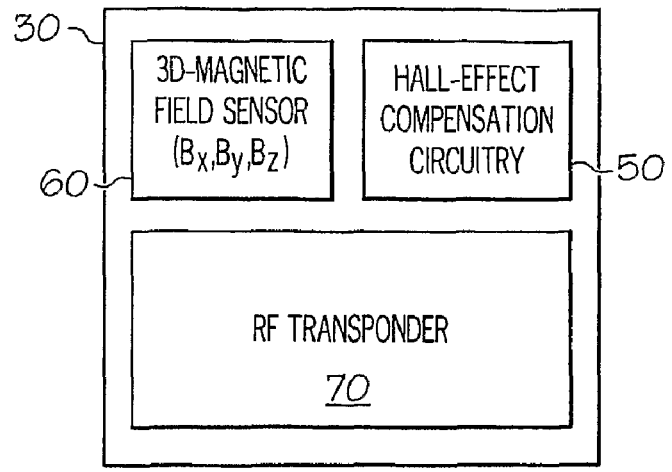
FIG. 2 is a block diagram of the sensor device's system architecture according to one embodiment of the present invention.

FIG. 2 is a block diagram of the sensor device's system architecture that is composed of three main functional blocks: the three-dimensional Hall-effect sensor 60, compensation circuitry 50 and the radio frequency circuitry 70 for receiving power and transmitting sensor data to the data processing device. The sensing device(s) 30 can be placed in a fixed location outside the eye, or fixed within the eye at a location that does not move in unison with the ciliary body. If implanted within the eye, the device 30 will be coated with a biocompatible material to prevent adverse reactions with the surrounding tissue.

Advances in semiconductor processing techniques have enabled the integration of many circuit functions onto a single substrate. A three-dimensional Hall-effect sensor will be used, similar to one's previously defined, to simultaneously measure the magnetic field strength in all three coordinate dimensions: x, y and z. The sensing device, by result of the Hall-effect, will transduce or convert magnetic energy of the component magnetic field magnitudes ($B_x$, $B_y$, and $B_z$) into corresponding voltage signals ($V_x$, $V_y$, and $V_z$), respectively. Other functions will be integrated to augment and enhance the Hall-effect sensor operation such as, but not limited to, biasing, amplification, offset cancellation and temperature stabilization by newly created implementations or methods previously described.

The RF transponder circuitry 70 is responsible for the wireless power supply reception and management and, also, transmission of the voltage data signals ($V_x$, $V_y$, and $V_z$) by similar, but not limited to, previously defined methods. The data voltage signals will be transmitted from the SD 30 to the DPD 40 for further processing. With this type of RF transponder 70 functionality, the SD 30 is able to operate free of batteries and physical connections which is a critical feature for implanted devices.

Data Processing Device (DPD)

Figure 3:
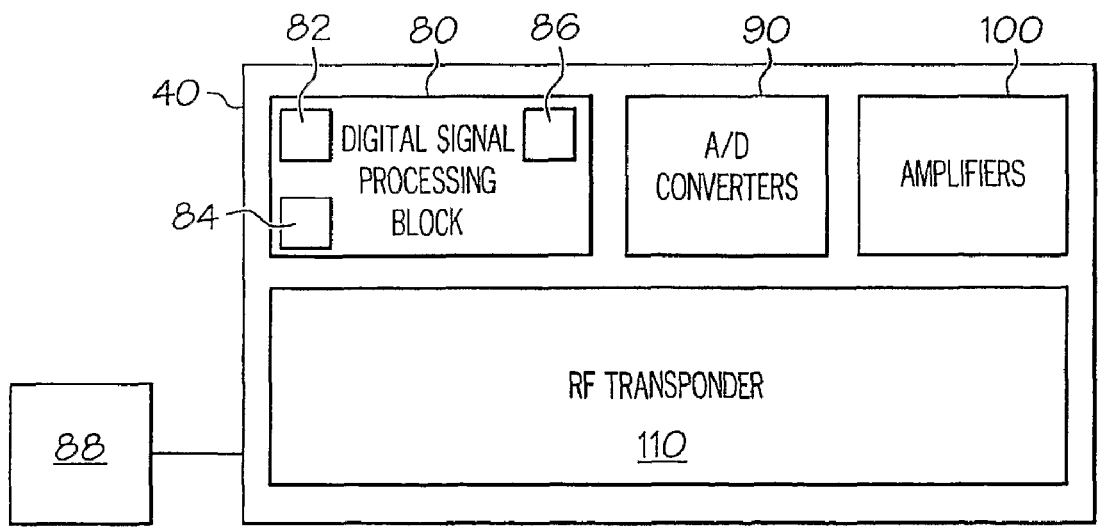
FIG. 3 is a block diagram of the data processing device's system architecture according to one embodiment of the present invention.

FIG. 3 is a block diagram of the data processing device 40's system architecture. The data processing device 40 is composed of four main functional blocks, the RF transponder 110, amplification 100, analog-to-digital conversion 90, and the digital signal processing block 80. The DPD 40 resides in a fixed location outside the eye and does not need to fulfill any biocompatibility requirements. In addition, it can be created using industry standard application specific integrated circuit (ASIC) design and CMOS manufacturing processes. The DPD 40 will have dedicated external power supplies and use industry standard device packages.

The RF transponder circuitry 110 provides the complement function to that found in the SD 30. It transmits power to the SD 30 and receives data from the SD 30 by similar, but not limited to, previously defined methods. Once the three-dimensional sensor data from the SD 30 is received, the signals are passed to the next functional block for amplification 100.

The amplification section 100 is a pre-processing step to increase the amplitude of the sensed signals to enable greater resolution in determining the magnet(s) 20 position(s). The amplified output signals will then be sent to the analog-to-digital (A/D) conversion block 90.

The A/D block 90 converts the analog signals to digital representations to simplify the signal processing implementation. The A/D circuitry 90 will be designed to have a minimum of six bits of resolution and a maximum sampling rate determined by the rate of signal transmission from the SD 30 to the DPD 40. The digital output signals are then sent to the digital signal processing block 80.

The digital signal processing block 80 will contain embedded memory 82 and custom logic 84 to perform filtering algorithms and calculate the position of the magnet 20, velocity and acceleration based on the received sensor data. The digital signal processing block 80 will also contain control circuitry 86 to synchronize the receive and transmit function of the RF transponder 110, clock generation, power on reset and other functions to maintain proper operation of the device. The output signals from the DPD 40 can then be sent to a visual display device 88 such as an LED device or a computer. The DPD 40 output can also be sent to another device to act as a feedback or control signal.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined above. More specifically, although some aspects of the present invention are identified herein as preferred or particularly advantageous, it is contemplated that the present invention is not necessarily limited to these preferred aspects of the invention.

The invention claimed is:

1. A sensing system to detect and determine magnitude and direction of ciliary body movement within an eye of a patient, said system comprising:
a permanent magnet adapted for positioning in the ciliary body;
a sensing device adapted for positioning adjacent to the ciliary body and configured to detect three-dimensional displacement of the permanent magnet relative to the sensing device via movement of the ciliary body during accommodation and disaccommodation; and
a data processing device configured to determine magnitude and direction of the ciliary body movement based on the displacement of the permanent magnet detected by the sensing device and configured to dynamically calculate velocity and acceleration of the ciliary body movement during accommodation and disaccommodation;
wherein said sensing device is adapted to be powered wirelessly.

2. The sensing system according to claim 1 wherein said permanent magnet is a rare-earth permanent magnet.

3. The sensing system according to claim 1 wherein said permanent magnet is adapted to be positioned in the ciliary body between circular fibers of ciliary muscle and ciliary processes.

4. The sensing system according to claim 1 wherein said permanent magnet has a thin layer of biocompatible material to eliminate oxidation and adverse effects to the ciliary body.

5. The sensing system according to claim 1 wherein said permanent magnet has a metal layer selected from nickel, zinc, and aluminum.

6. The sensing system according to claim 1 wherein said permanent magnet has at least one magnetic orientation providing a fixed magnetic field with regard to a single magnet plane or axis.

7. The sensing system according to claim 1 wherein said sensing device is configured to detect change in the magnetic field of the permanent magnetic due to the movement of the ciliary body.

8. The sensing system according to claim 1 wherein said sensing device is configured to detect change in the magnetic field of the permanent magnetic due to the movement of the ciliary body such that three-dimensional magnetic field orientations and magnitudes of the position of the magnet relative to the sensor can be determined at any point in time.

9. The sensing system according to claim 1 wherein said sensing device comprises a three-dimensional Hall-effect sensor, compensation circuitry, and radio frequency circuitry for receiving power and transmitting sensor data to the data processing device.

10. The sensing system according to claim 1 wherein said data processing device comprises a RF transponder, amplification circuitry, analog-to-digital conversion circuitry, and digital signal processing circuitry.

11. The sensing system according to claim 1 wherein said sensing device and said data processing device are application specific integrated circuit (ASIC) devices.

12. The sensing system according to claim 1 wherein said sensing device and said data processing device are CMOS based devices.

13. The sensing system according to claim 1 wherein said data processing device comprises a digital signal processing circuitry having embedded memory and custom logic to perform filtering algorithms and to calculate position, velocity, and acceleration of the permanent magnet based on received sensor data from the sensing device.

14. The sensing system according to claim 1, wherein said date processing device generates a feedback control signal to an intraocular device.

15. A method of detecting and determining magnitude and direction of ciliary body movement within an eye of a patient using a sensing system comprising:
   a permanent magnet adapted for positioning in the ciliary body;
   a sensing device adapted for positioning adjacent to the ciliary body and configured to detect three-dimensional displacement of the permanent magnet relative to the sensing device via movement of the ciliary body during accommodation and disaccommodation; and
   a data processing device configured to determine magnitude and direction of the ciliary body movement based on the displacement of the permanent magnet detected by the sensing device and configured to dynamically calculate velocity and acceleration of the ciliary body movement during accommodation and disaccommodation;
   wherein said sensing system is powered wirelessly.

16. The method of claim 15 wherein the sensing device comprises a three-dimensional Hall-effect sensor, and said method further comprises sensing magnetic field strength of the permanent magnetic in all three coordinate dimensions (x, y and z).

17. A method of determining ciliary body movement within an eye, said method comprises:
   positioning a permanent magnet in the ciliary body such that disaccommodation and accommodation of the ciliary body is detectable;
   positioning a wirelessly powered sensing device adjacent the ciliary body;
   detecting three-dimensional displacement of the permanent magnet relative to the sensing device via movement of the ciliary body during accommodation and disaccommodation;
   using a data processing device to determine magnitude and direction of the ciliary body movement based on the displacement of the permanent magnet detected by the sensing device;
   using a data processing device to dynamically calculate velocity and acceleration of the ciliary body movement during accommodation and disaccommodation based on the displacement of the permanent magnet detected by the sensing device.

18. The method of claim 17 wherein the sensing device is positioned at a fixed location that does not move in unison with the ciliary body.

19. The method of claim 18, wherein the sensing device is positioned outside the eye.

20. The method of claim 18, wherein the sensing device is positioned within the eye.

21. The method of claim 17, further comprising:
   generating a feedback control signal based on the displacement of the permanent magnet detected by the sensing device; and
   controlling an intraocular device with said feedback control signal.

* * * * *